United States Patent [19]

Nieuwland et al.

[11] 4,288,350

[45] Sep. 8, 1981

[54] PERFUME COMPOSITIONS CONTAINING DIALKYL DELTA-LACTONES

[75] Inventors: Kees N. Nieuwland, Amersfoort; Dirk K. Kettenes, Putten, both of Netherlands

[73] Assignee: Polak's Frutal Works B.V., Amersfoort, Netherlands

[21] Appl. No.: 134,010

[22] Filed: Mar. 26, 1980

Related U.S. Application Data

[63] Continuation of Ser. No. 858,502, Dec. 7, 1977, abandoned.

[30] Foreign Application Priority Data

Dec. 23, 1976 [GB] United Kingdom ............... 53707/76

[51] Int. Cl.$^3$ ........................... A61K 7/46; C11B 9/00
[52] U.S. Cl. .............................. 252/522 R; 260/343.5
[58] Field of Search ..................... 252/522 R

[56] References Cited

U.S. PATENT DOCUMENTS 2,526,702 10/1950 Smith .
2,576,901 11/1951 de Jong .
2,680,118 6/1954 Emerson et al. .
3,479,327 11/1969 Merijan et al. ...................... 424/65

FOREIGN PATENT DOCUMENTS 854503 11/1952 Fed. Rep. of Germany .
962429 4/1957 Fed. Rep. of Germany .

OTHER PUBLICATIONS

Chem. Ab. 62:14493, 1965; 49:176.

*Primary Examiner*—John F. Niebling
*Attorney, Agent, or Firm*—William S. Alexander

[57] ABSTRACT

Certain dialkyl delta-lactones are disclosed to be useful as perfumery ingredients.

7 Claims, No Drawings

PERFUME COMPOSITIONS CONTAINING DIALKYL DELTA-LACTONES

This is a continuation application Ser. No. 858,502, filed Dec. 7, 1977, now abandoned.

This invention relates to fragrance compositions and novel materials for use therein. More specifically, it relates to such compositions which contain as an olfactory ingredient a $\gamma,\gamma$-disubstituted-$\delta$-valerolactone having the structural formula

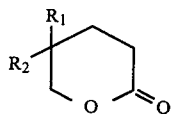

wherein $R_1$ and $R_2$ are the same or different alkyl or alkenyl radicals.

There is a continuing search for materials having useful perfumery fragrance characteristics. These materials are sought either as replacements for naturally occurring components or as totally new scents or odor notes in their own right. It is the purpose of this invention to provide a synthetic material having an odor reminiscent of that of costus oil.

Costus root oil is an essential oil obtained from the dried roots of "Saussurea lappa" growing in the Himalayan highlands. The oil is used in high-grade perfumes and has a very strong and tenacious odor, reminiscent of that of human hair. The oil is expensive and not always available, and since it is a natural product, its quality is not always consistent. Several grades of costus root oil available in the trade are known to cause allergic reactions in some individuals. A replacement is therefore desirable.

It is known that some $\gamma$-alkyl-$\gamma$-lactones, such as the series $\gamma$-nonalactone to $\gamma$-dodecalactone, are used as fragrance ingredients. Their odors vary gradually from coconut to fruity peach. Also $\delta$-alkyl-$\delta$-lactones, whose odors differ only in nuances from those of the $\gamma$-alkyl-$\gamma$-lactones, are known to the art. However, these do not appear to have found wide acceptance. So far as is known, the $\gamma,\gamma$-dialkyl-$\delta$-lactones have not heretofore been known as fragrance chemicals, although some of the compounds per se are not novel.

As stated, the $\gamma,\gamma$-disubstituted valerolactones which have been found useful according to this invention have the structural formula

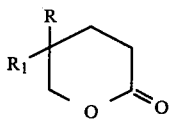

where R and $R_1$ are the same or different alkyl or alkenyl group. Preferably R and $R_1$ have 1 to 8 carbon atoms and most preferably R and $R_1$ have 1 to 8 carbon atoms with a total of 3 to 10 carbon atoms between them. So far as is known, the only members of this class synthesized or publicized to date are $\gamma,\gamma$-diethyl valerolactone and $\gamma$-ethyl-$\gamma$-n-butyl valerolactone.

Other typical compounds encompassed by the formula which are useful in fragrance compositions according to this invention and which are novel are $\gamma$-methyl-$\gamma$-propyl-$\delta$-valerolactone, $\gamma$-methyl-$\gamma$-1-propenyl-$\delta$-valerolactone, $\gamma$-ethyl-$\gamma$-1butenyl-$\delta$-valerolactone, $\gamma$-propyl-$\gamma$-pentyl-$\delta$-valerolactone, $\gamma$-propyl-$\gamma$-1-pentenyl-$\delta$-valerolactone, $\gamma$-butyl-$\gamma$-hexyl-$\delta$-valerolactone and $\gamma$-butyl-$\gamma$-1-hexenyl-$\delta$-valerolactone.

The $\gamma,\gamma$-dialkyl-$\delta$-lactones can be prepared by methods known to the art. The following reaction schemes set forth a preferred method. (See Bruson and Riener, J.A.C.S. 66, page 56 (1944). In the equations R and $R_1$ are as defined above.

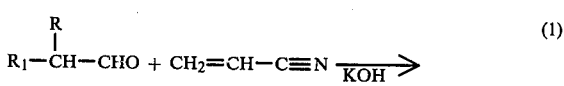

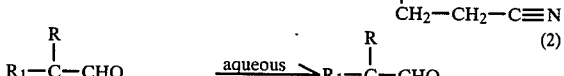

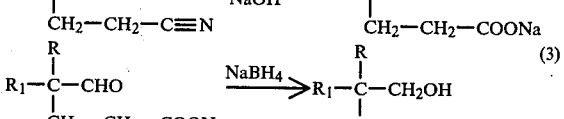

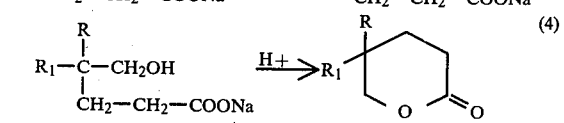

Alternatively, Step (1) of the above reaction scheme can be as follows where $R_2$ is hydrogen or a 1 to 6 carbon alkyl group.

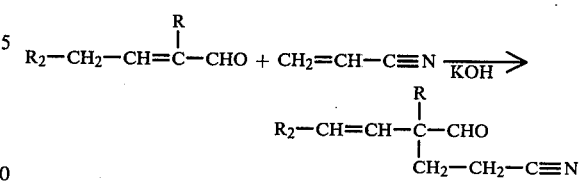

$R_2$-CH=CH- can be seen to fit the definition of R and $R_1$ above.

The reduction of the carbonyl group to a hydroxyl group, accomplished via $NaBH_4$ in Step (3) of the reaction scheme, can also be accomplished by means of hydrogen and Raney nickel. This method is especially useful when it is also desired to hydrogenate a carbon-to-carbon double bond in one of the substituent groups. If it is desired to retain the double bond in the alkenyl group, $NaBH_4$ is the preferred reduction agent. It is also feasible to use the $NaBH_4$ reduction followed by hydrogenation of the alkenyl double bond when the substituent groups are to be saturated.

The $\gamma,\gamma$-dialkyl-$\delta$-valerolactones can be used alone as fragrances per se or they can be used as components of a fragrance composition. The term "fragrance composition" is used to denote a mixture of compounds including, for example, natural oils, synthetic oils, alcohols, aldehydes, ketones, esters, lactones, ethers, hydrocarbons and other classes of chemical compounds which are admixed so that the combined odors of the individual components produce a pleasant or desired fragrance. Such fragrance compositions or the novel compounds of this invention can be used in conjunction with carriers, vehicles or solvents containing also, as needed, dispersants, emulsifiers, surface-active agents, aerosol propellants and the like.

In fragrance compositions the individual components contribute their particular olfactory characteristics, but the overall effect of the composition is the sum of the effect of each ingredient. Thus, the γ,γ-dialkyl-δ-valerolactones of this invention can be used to alter, enhance, or reinforce the aroma characteristics of the other natural or synthetic materials making up the fragrance composition, for example, by highlighting or moderating the olfactory reaction contributed by another ingredient or combination of ingredients.

The amount of γ,γ-dialkyl-δ-valerolactone which will be effective depends on many factors including the other ingredients, their amounts and the effects which are desired. It has been found that as little as 0.01 to 5% by weight of compounds of this invention can be used to alter the effect of a fragrance composition. The amount employed will depend on considerations of cost, nature of end product, the effect desired in the finished product, and the particular fragrance sought.

The compounds disclosed herein can be used in a wide variety of applications such as, e.g., detergents and soaps; space deodorants; perfumes, colognes; after-shave lotions; bath preparations such as bath oil and bath salts; hair preparations such as lacquers; brilliantines, pomades and shampoos; cosmetic preparations such as creams, deodorants, hand lotions, and sun screens; powders such as talcs, dusting powders, face powder; as masking agents, e.g., in household products such as bleaches, and in technical products such as shoe polish and automobile wax.

The following examples are given for the purpose of illustrating the invention.

EXAMPLE 1

Preparation of γ-methyl-γ-n-propyl-δ-Valerolactone

Thirty-three and one-tenth (33.1) g. acrylonitrile was added dropwise in the course of one hour to a stirred mixture of 50 g. (0.499 mole) 2-methylpentanal and 1.3 g. 50% potassium hydroxide solution. The reaction temperature was maintained at 55° C. After complete addition of the acrylonitrile, the mixture was stirred for three and a half hours at 55° C., cooled, taken up in ether and washed with water until neutral. After drying and evaporation of the solvent, the product, 2-(beta-cyanoethyl)-2-methylpentanal, distilled at 89°–90° C. at 0.6 mm. Yield 59.0 g. (77%); $n_D^{20}$ 1.4460.

A mixture of 50 g. (0.326 mole) of 2-(beta-cyanoethyl) 2-methylpentanal, 27.3 g. (0.489 mole) potassium hydroxide and 150 ml. water was stirred for four and a half hours at reflux temperature. The reaction mixture was cooled to 20° C. and a solution of 13.6 g. (0.359 mole) sodium borohydride in 75 ml. water was added. The reaction temperature rose to 50° C. Stirring was continued for one and a half hours during which period the temperature dropped to 20° C. again. The reaction mixture was acidified with dilute hydrochloric acid. The oil was taken up in ether, washed with water and dried. Distillation yield 39.5 g. (78%) γ-methyl-γ-propyl-δ-valerolactone boiling at 85°–86° C. at 0.6 mm; $n_D^{20}$ 1.4599. This oil exhibits a greenish, cumarinic, coconut-like hairy odor.

EXAMPLE 2

Preparation of γ-ethyl-γ-n-butyl-δ-valerolactone 2-(Beta-cyanoethyl)-2-ethylhexanal was prepared from 2-ethylhexanal and acrylonitrile analogous to the procedure described in Example 1 for 2-(beta-cyanoethyl)2-methylpentanal. Yield 81% of the product boiling at 112°–114° C. at 0.5 mm.; $n_D^{20}$ 1.4538. This product was converted to γ-ethyl-γ-n-butyl-δ-valerolactone as described in Example 1 for γ-methyl-γ-n-propyl-δ-valerolactone. Yield 78%, product boils at 104°–105° C. at 0.6 mm.; $n_D^{20}$ 1.4652 and exhibits a hairy, lactonic, fatty, costus-like odor.

EXAMPLE 3

Preparation of γ-ethyl-γ-1-butenyl-δ-valerolactone 2-(Beta-cyanoethyl)-2-ethyl-3-hexanal was prepared from 2-ethyl-2-hexenal and acrylonitrile according to the procedure of Example 1. Yield 57% of the product, boiling at 102°–112° C. at 0.6 mm.; $n_D^{20}$ 1.4681. The product was converted to γ-ethyl-γ-1-butenyl-δ-valerolactone as described in Example 1 for γ-methyl-γ-n-propyl-δ-valerolactone. Yield 67% of the product boiling at 104°–105° C. at 1 mm.; $n_D^{20}$ 1.4772. Odor description: costus-like, hairy, lactonic.

EXAMPLE 4

Preparation of γ-butyl-γ-1-hexenyl-δ-valerolactone 2-(Beta-cyanoethyl)-2-butyl-3-octenal was prepared from 2-butyl-2-octenal and acrylonitrile analogously to the preparation of 2-(beta-cyanoethyl)2-methylpentanal as described in Example 1. Yield 38% of the product boiling at 143°–148° C. at 0.6 mm.; $n_D^{20}$ 1.4754. Saponification and reduction as described in Example 1 gave γ-butyl-γ-1-hexenyl-δ-valerolactone boiling at 125°–127° C. at 0.4 mm. Yield 54%; $n_D^{20}$ 1.4754. Odor description: fatty, greenishlike butyl alcohol.

EXAMPLE 5

Preparation of γ-butyl-γ-n-hexyl-δ-valerolactone

Nine and five-tenths (9.5) g. (0.04 mole) γ-butyl-γ-1-hexenyl-δ-valerolactone as prepared in Example 4 was hydrogenated at atmospheric pressure in 100 ml. ethanol with 1 g. 10% palladium on charcoal. After uptake of the theoretical amount of hydrogen the catalyst was removed by filtration. Distillation yielded 7.5 g. (78%) γ-butyl-γ-n-hexyl-δ-valerolactone boiling at 130°–132° C. at 0.4 mm.; $n_D^{20}$ 1.4652.

Odor description: costus-like, fatty, hairy.

EXAMPLE 6

Preparation of γ,γ-diethyl-δ-valerolactone

γ,γ-Diethyl-δ-valerolactone was prepared from 2-ethylbutanal and acrylonitrile analogous to Example 1. Yield of the intermediate 2-(beta-cyanoethyl)2-ethylbutanal 72%, boiling at 100°–101° C. at 1.5 mm.; $n_D^{20}$ 1.4502. Yield of γ,γ-diethyl-δ-valerolactone from this intermediate 78%, boiling at 93°–94° C. at 0.8 mm.; $n_D^{20}$ 1.4650. Odor description: fruity, lactonic, cumarinic.

EXAMPLE 7

Preparation of γ-propyl-γ-1-pentenyl-δ-valerolactone

γ-Propyl-δ-1-pentenyl-δ-valerolactone was prepared from 2-propyl-2-heptenal and acrylonitrile analogous to Example 1. Yield of 2-(beta-cyanoethyl)-2-propyl-3-heptenal 38%, boiling at 118°–120° C. at 0.6 mm.; $n_D^{20}$ 1.4640. Yield of γ-propyl-γ1-pentenyl-δ-valerolactone from this intermediate 40%, boiling at 107°–110° C. at 0.4 mm.; $n_D^{20}$ 1.4749.

Odor description: orris-like, fatty, costus-like.

EXAMPLE 8

Preparation of γ-propyl-γ-n-pentyl-δ-valerolactone

γ-Propyl-γ-n-pentyl-δ-valerolactone was prepared from γ-propyl-γ-1-pentenyl-δ-valerolactone of Example 7 by hydrogenation analogous to Example 5. Yield 94%, boiling at 116°–118° C. at 0.5 mm.; $n_D^{20}$ 1.4647.

Odor description: fatty, lactonic, orris-like, costus-like.

EXAMPLE 9

Perfume composition containing γ-ethyl-γ-n-butyl-δ-valerolactone

| | |
|---|---|
| 100 g. | tert-butylcyclohexyl acetate |
| 10 | geranonitrile |
| 10 | cyclamen aldehyde |
| 20 | tricyclo[5.2.1.0$^{2,6}$]dec-3-en-8-yl acetate |
| 5 | methyl coumarine |
| 50 | cedarwood oil |
| 45 | coumarine |
| 10 | isoeugenol |
| 10 | eugenol |
| 20 | mousse d'arbre decoloree |
| 10 | undecylenic aldehyde 10% solution |
| 10 | methylnonylacetaldehyde 10% solution |
| 20 | dihydromyrcenol |
| 60 | geraniol |
| 40 | citronellol |
| 80 | benzyl salicylate |
| 30 | 2-methyl-3-(4-t-butylphenyl)propanal |
| 10 | ethylvanilline - 10% solution |
| 10 | Schiff's base of indole and hydroxycitronellal-10% solution |
| 100 | 2-hexyl-3-carbomethoxycyclopentanone |
| 50 | 4-(and 3) (4-hydroxy-4-methylpentyl)-3-cyclohexenecarbaldehyde |
| 55 | benzophenone |
| 10 | trichloromethylphenylcarbinyl acetate |
| 50 | musk ketone |
| 20 | 3,5,5,6,8,8-hexamethyl-5,6,7,8-tetrahydro-2-acetonaphthone |
| 10 | Schiff's base of hydroxycitronellal and methyl anthranilate |
| 5 | methyl-beta-naphthyl ketone |
| 20 | Beta-phenylethyl ethyl acetal of acetaldehyde |
| 5 | methylenedioxyphenylbutanone |
| 15 | 2-methyl-3-(3,4-methylenedioxyphenyl)propanol |
| 10 | γ-ethyl-γ-n-butyl-δ-valerolactone |
| 900 g. | |

The addition of the γ-ethyl-γ-n-butyl-δ-valerolactone (10 g.) to the mixture results in a very clear and desirable difference, the effect going in an animalic lactonic direction.

EXAMPLE 10

Perfume composition containing gamma-ethyl-gamma-1-butenyl-delta-valerolactone (Men's Fragrance)

| | |
|---|---|
| 375 g. | Bergamot oil |
| 150 | Acetylated guaiac wood oil |
| 150 | Gamma-methylionone |
| 15 | Methyl-3,6-dimethyl resorcylate |
| 55 | 2-Hexyl-3-carbomethoxycyclopentane |
| 15 | Cis-3-hexenyl isobutyrate |
| 75 | Vertofix Coeur (IFF) |
| 45 | 4-(and 3) (4-Hydroxy-4-methylpentyl)-3-cyclohexene carbaldehyde |
| 75 | 6-Oxa-1,1,2,3,3,8-hexamethyl-2,3,5,6,7,8-hexahydro-1H-benz(F) indene |
| 30 | Vetiveryl acetate |
| 15 | Gamma-ethyl-gamma-1-butenyl-delta-valerolactone |

The addition of the 15 g. gamma-ethyl-gamma-1-butenyl delta-valerolactone results in a clear and desirable difference, the effect being in an animalic-leathery direction.

What we claim and desire to protect by Letters Patent is:

1. A fragrance composition comprising, in combination with other olfactorily active materials, an odor-modifying amount of a substituted δ-valerolactone having the structural formula

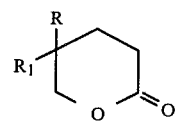

where R and R$_1$ are the same or different alkyl or alkenyl groups.

2. A fragrance composition comprising, in combination with other olfactorily active ingredients, an odor-modifying amount of a substituted δ-valerolactone having the structural formula

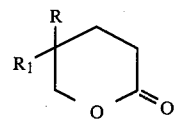

where R and R$_1$ are the same or different alkyl or alkenyl group having 1 to 8 carbon atoms.

3. A fragrance composition comprising, in combination with other olfactorily active materials, an odor-modifying amount of a substituted δ-valerolactone having the structural formula

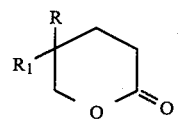

wherein R and R$_1$ are the same or different alkyl or alkenyl groups having 1 to 8 carbon atoms and having a total of 3 to 10 carbon atoms between them.

4. A fragrance composition in accordance with claim 3 wherein the δ-valerolactone is γ-ethyl-γ-n-butyl-δ-valerolactone.

5. A perfume comprising a substituted δ-valerolactone having the structural formula

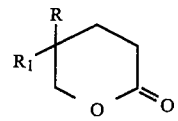

wherein R and R$_1$ are the same or different alkyl or alkenyl groups having 1 to 8 carbon atoms and having a total of 3 to 10 carbon atoms between them, said δ-valerolactone being incorporated into a suitable carrier.

6. The perfume of claim 5 wherein the δ-valerolactone is γ-ethyl-γ-n-butyl-δ-valerolactone.

7. A fragrance composition comprising, in combination with other olfactorily active ingredients, an odor-modifying amount of γ-ethyl-γ-1-butenyl-δ-valerolactone.

* * * * *